United States Patent [19]

Thomas

[11] Patent Number: 4,906,242

[45] Date of Patent: Mar. 6, 1990

[54] APPARATUS FOR PREVENTING THE SPREADING OF ACQUIRED IMMUNE DEFICIENCY SYNDROME (AIDS)

[76] Inventor: Herman A. Thomas, 2221 Orange Blossom La., Bradenton, Fla. 33507

[21] Appl. No.: 199,539

[22] Filed: May 27, 1988

Related U.S. Application Data

[63] Continuation-in-part of Ser. No. 72,677, Jul. 18, 1987, abandoned, and a continuation-in-part of Ser. No. 91,455, Aug. 31, 1987, abandoned.

[51] Int. Cl.⁴ .................................................. A61F 5/44
[52] U.S. Cl. ..................................... 604/353; 128/844; 128/918
[58] Field of Search ........................... 128/844; 4/144.3; 604/327, 331, 347, 349–353

[56] References Cited

U.S. PATENT DOCUMENTS

| 2,484,356 | 10/1949 | Ribeiro et al. | 604/347 |
| 2,610,630 | 9/1952 | Crew | 604/347 |
| 4,073,295 | 2/1978 | Laufbahn | 604/353 |

FOREIGN PATENT DOCUMENTS 355426 10/1905 France ................................ 604/349

Primary Examiner—Jerome L. Kruter
Attorney, Agent, or Firm—Gifford, Groh, Sprinkle, Patmore and Anderson

[57] ABSTRACT

A device to prevent the spreading of Acquired Immune Deficiency Syndrome virus or AIDS comprises an elastic belt worn around the hips or mid-body portion of a male person. The belt has separated ends and button and button hole for fastening the ends together. A condom is mounted to the belt by being secured between the button and the button hole.

2 Claims, 1 Drawing Sheet

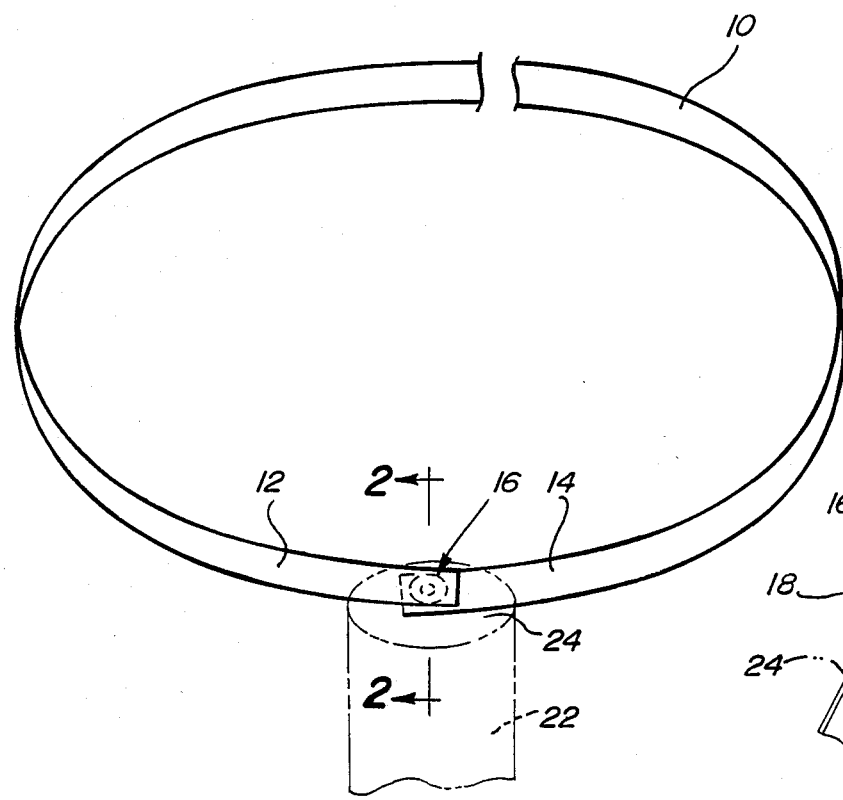
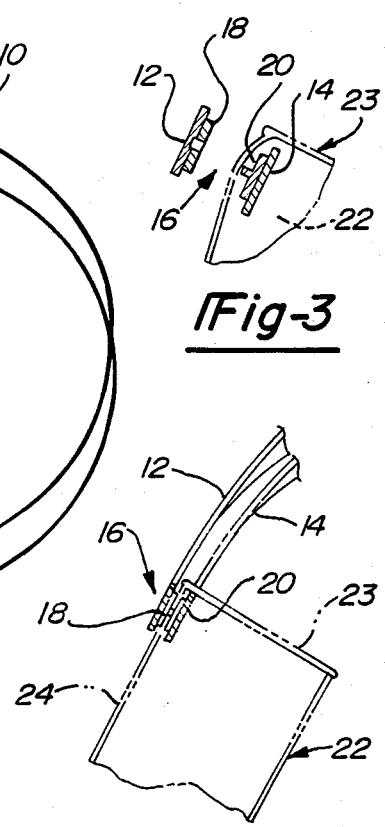
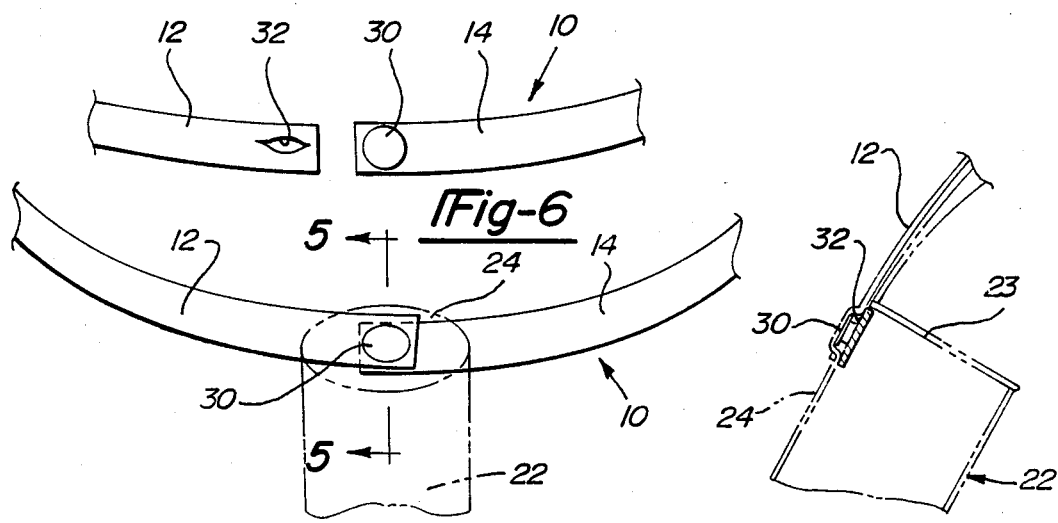
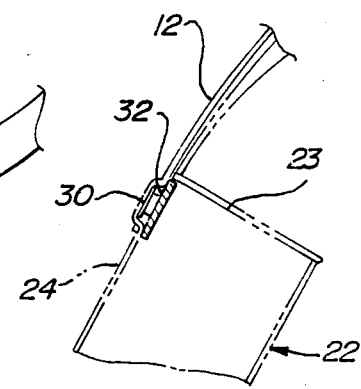

APPARATUS FOR PREVENTING THE SPREADING OF ACQUIRED IMMUNE DEFICIENCY SYNDROME (AIDS)

CROSS REFERENCE TO RELATED APPLICATION

This application is a continuation-in-part of application Ser. No. 072,677, filed July 18, 1987 now abandoned and 091,455, filed Aug. 31, 1987 now abandoned.

BACKGROUND OF THE INVENTION

The present invention is concerned with public health and welfare, and, as such, is an important contribution to the prevention of the spreading of Acquired Immune Deficiency Syndrome, commonly called AIDS virus.

AIDS, at the present time, is an alarming public health problem and there is no present cure for this terrible disease. In its most severe form, AIDS is a complete collapse of a person's natural immune system that leaves the person without resistance to infections.

There is no evidence at present that AIDS is spread casually. Sexual contact, blood contact, and the transmission from an infected mother to a child account for almost all of the presently known causes of AIDS patients.

Any individual with multiple sexual partners, or any partner that may have had multiple sexual partners is a risk for AIDS.

People with AIDS are largely members of certain groups known as "high risk" groups. Such persons are mainly male homosexuals or bisexual males, and the disease is more frequent among men who have a large number of sexual partners.

The AIDS virus is transmitted through body fluids, specifically semen during sexual intercourse and blood through sharing hypodermic needles and syringes.

Because the AIDS virus is easily transmitted by semen during sexual intercourse, it is proposed to apply to the erected phallus a prophylactic device, such as a condom, whereby semen when it is ejaculated is caught in the device. But, in some instances, the condom becomes separated from the phallus and the semen is not caught in the condom. Wherefore, the effect is to transmit the AIDS virus unintentionally.

Applicant's previous disclosures disclose means to aid in preventing the condom from becoming separated from the phallus during sexual intercourse.

SUMMARY OF THE INVENTION

The present invention is an improvement of my previously disclosed device and comprises an elastic belt worn by a male person, and in one preferred embodiment of the invention, the belt has a button and a button hole which fastens the ends of the belt together and which captures the upper portion of a condom, thereby preventing the condom from becoming separated from the phallus during and after sexual intercourse.

In another preferred embodiment a belt is provided with a snap assembly having a female portion on one end of the belt and a male portion on the other end. The assembly is snapped together with an upper portion of the condom captured between the male portion and the female portion of the snap.

It is a primary object of the present invention then to provide an improved apparatus that prevents a condom from becoming separated from an erected phallus during and after sexual intercourse.

The many objects and features as well as advantages of the present invention will become to those skilled in the art from the following description of the best mode contemplated for practicing the invention when it is read in conjunction with the accompanying drawings wherein like numerals refer to like or equivalent parts.

BRIEF DESCRIPTION OF THE DRAWINGS

FIG. 1 is a front elevation view showing one preferred embodiment of the present invention.

FIG. 2 is a partial sectional view along line II—II of FIG. 1.

FIG. 3 is a partial sectional view similar to FIG. 2 but illustrating the snap assembly in an open condition;

FIG. 4 is a partial elevational view similar to FIG. 1, but illustrating another preferred embodiment of the present invention;

FIG. 5 is a partial sectional view taken along line V—V of FIG. 4; and

FIG. 6 is a partial elevational view of the belt of FIG. 4 in an unfastened condition.

DETAILED DESCRIPTION OF THE PRESENT INVENTION

Referring to FIG. 1, a belt 10 is adapted to surround the hips and mid-body of a male person (not shown). The belt 10 is preferably an elastic material having normally separated ends 12 and 14. A snap assembly 16 includes a female portion 18 and a male portion 20 which snap together to permit the belt 10 to be fastened about the user. The belt 10 can best be seen in the snapped together condition in FIG. 2.

A condom 22 is fastened to the belt 10 by placing the upper portion 24 of the condom 22 between the female portion 18 and the male portion 20 before snapping the assembly 16 together to thereby capture the condom 22 between the snapp assembly 16. The condom 22 includes an upper ring 23 peripherally fitted about its upper end.

FIGS. 3, 4 and 5 illustrate another preferred embodiment of the present invention as including an elastic belt 10 having normally separated ends 12 and 14. A button 30 is provided at one end 12 of the belt 10 and a button hole 32 is provided at the other end 14 so that inserting the button 30 through the button hole 32 in the normal fashion fastens the ends 12 and 14 of the belt 10 together, preferably about the hips and mid-body of a male user.

FIG. 3 illustrates the ends 12 and 14 of the belt 10 fastened together and FIG. 5 illustrates the belt 10 before the button 30 is inserted through the button hole 32 to fasten the belt together.

In the embodiment of FIGS. 3–5 the condom 22 is fastened to the belt by placing the upper portion of the condom 22 over the button 30 before inserting the button 30 through the button hole 32. This can best be seen in FIG. 4.

Thus during the sexual act with either the embodiments of FIGS. 1–2 and FIGS. 3–5 the condom 22 is held in place by reason of it being secured to the belt 10.

When the sexual act has been completed, the condom 22 can be readily removed from the belt 10 by either unsnapping the snap assembly 16 or by unbuttoning the button 30. The condom 22 can then, of course, be safely disposed of.

From the foregoing description of the preferred embodiments of the invention, and from the improvement therein, those who are skilled in the art of the present invention will recognize its many features and advantages. Among the many features and advantages the following are significant:

That the condom is secured to the belt during sexual intercourse and after ejaculation, the condom will not slip off the phallus when it is withdrawn;

That the body of the male person is not exposed to fluids that may carry AIDS virus that could infect such person;

That the present invention is relatively inexpensive and is useful in promoting public health and welfare;

That the belt of the invention is made of elastic material that hugs the hip portion of the male person tightly, thereby preventing the belt from slipping off the hip portion of the wearer;

That the belt is elastic and easily fitted to the hip portion of a male person of any size; and That the condom can be easily and quickly attached to the belt and detached therefrom as easily.

Although the present invention has been described with a certain degree of particularity, it is understood that other modifications may be made therein without departing from the scope of the invention as defined by the following claims.

I claim:

1. A device for aiding in the prevention of the spread of the Acquired Immune Deficiency Syndrome, commonly called AIDS, virus comprising:

a belt having separate ends including a male end and a female end, said belt surrounding the mid-body and hip portion of a male person;

means for attaching said male end of said belt to said female end, said means including a male portion provided at said male end and a female portion provided at said female end, said male portion and said female portion being interconnectable; and a conventional condom having an upper portion, said upper portion of said condom having an open end, said open end having a ring peripherally fitted thereabout, said upper portion of said condom mounted to said belt by said attaching means whereby said upper portion of said condom is captured between said male portion and said female portion of said belt;

said male portion comprising a male snap assembly carried by said male end of said belt and said female portion comprising a female snap assembly carried by said female end of said belt, said male and female portions being snappingly attachable when said male portion is received by said female portion for releasably attaching an end of said belt to the other end of said belt;

said upper portion of said condom extending between said male portion and said female portion to capture said upper portion of said condom between said male portion and said female portion when said snap assembly is snapped together.

2. The device as defined in claim 1 in which said attaching means comprises a button carried by said male end of said belt and said female portion comprising, a button hole provided on the female end of said belt and adapted to receive said button to attach one end of said belt to the other end;

said upper portion of said condom extending over said button prior to insertion of said button into said button hole whereby said upper portion of said condom is captured between said button and said button hole.

* * * * *